United States Patent [19]
Kyte

[11] Patent Number: 5,896,868
[45] Date of Patent: Apr. 27, 1999

[54] FLUORIDE/PEROXIDE DENTAL FLOSS

[76] Inventor: Ricky R. Kyte, 1345 Camden Ct., Mobile, Ala. 36695

[21] Appl. No.: 08/697,916

[22] Filed: Sep. 3, 1996

[51] Int. Cl.$^6$ .................................................. A61C 15/00
[52] U.S. Cl. .......................... 132/322; 222/192; 118/420
[58] Field of Search ........................ 132/322, 324, 132/325; 222/192, 135; 118/412, 420, 36, 423

[56] References Cited

U.S. PATENT DOCUMENTS

| | | | |
|---|---|---|---|
| 1,542,243 | 6/1925 | Heinzelman | 132/325 |
| 2,349,005 | 5/1944 | Roe | 222/135 |
| 3,830,247 | 8/1974 | Kaphalakos . | |
| 3,863,655 | 2/1975 | Smith | 132/322 |
| 3,893,412 | 7/1975 | Louch et al. | 118/420 |
| 3,902,510 | 9/1975 | Roth | 132/322 |
| 4,673,106 | 6/1987 | Fishman | 222/192 |
| 4,827,951 | 5/1989 | Grussmark | 132/324 |
| 4,949,874 | 8/1990 | Fiedler et al. | 222/135 |
| 5,280,796 | 1/1994 | Rosenberger . | |
| 5,353,820 | 10/1994 | Suhonen . | |
| 5,357,990 | 10/1994 | Suhonen . | |
| 5,423,337 | 6/1995 | Ahlert . | |
| 5,507,414 | 4/1996 | Ong | 222/192 |

*Primary Examiner*—Gene Mancene
*Assistant Examiner*—Eduardo C. Robert
*Attorney, Agent, or Firm*—Patent & Trademark Services; Joseph H. McGlynn

[57] ABSTRACT

A container for dental floss which has dual chambers, one for a solution containing fluoride and another for peroxide. Each chamber has an aperture for applying the solution in each chamber to the floss, and a plunger for pushing the solution through the apertures.

15 Claims, 1 Drawing Sheet

FLUORIDE/PEROXIDE DENTAL FLOSS

BACKGROUND OF THE INVENTION

This invention relates, in general, to containers for dental floss, and, in particular, to containers for dental floss which apply an antiseptic solution to the floss.

DESCRIPTION OF THE PRIOR ART

In the prior art various types of dental floss containers have been proposed. For example, U.S. Pat. No. 3,830,247 discloses a container for dental floss that has a reservoir of antiseptic solution that the floss must move through before it can be removed from the container.

U.S. Pat. No. 5,280,796 discloses a dental floss coated with a phenol derivative compound removably fixed thereon by a binder such as wax.

U.S. Pat. No. 5,353,820 discloses a flavored interproximal dental cleaning device having an open porous brush portion with matrix particles comprising flavored particles encapsulated in a water solution.

U.S. Pat. No. 5,357,990 discloses a dental floss coated with a flavored compound.

U.S. Pat. No. 5,423,337 discloses a dental floss having a wax coating impregnated with a nascent oxygen generating agent such as calcium peroxide.

While the use of dental floss has been known as an effective agent in fighting tooth decay, it has only recently become widely used. Dental floss is manufactured and sold in thread form and is used to clean particles of food lodged between the teeth. When food particles lodge between the teeth, they immediately begin to break down. When these partially broken down particles are removed, such as by brushing or flossing, they leave a residue of material which tends to promote tooth decay.

It has been recently discovered that merely brushing or flossing is not sufficient to prevent tooth decay. In order to help prevent tooth decay, patents such as U.S. Pat. No. 3,830247 have devised ways to add an antiseptic solution to the dental floss. However, it has recently been found that the most effective solution is a combination of fluoride and peroxide. Until now, there has been no way to apply these two ingredients to dental floss.

SUMMARY OF THE INVENTION

The present invention comprises a container for dental floss which has dual chambers, one for a solution containing fluoride and another for peroxide. Each chamber has an aperture for applying the solution in each chamber to the floss, and a plunger for pushing the solution through the apertures.

It is an object of the present invention to provide an improved container for dental floss.

It is an object of the present invention to provide an improved container for dental floss which places an effective solution to the floss to help fight tooth decay.

These and other objects and advantages of the present invention will be fully apparent from the following description, when taken in connection with the annexed drawings.

DESCRIPTION OF THE PREFERRED EMBODIMENT

Figure 1:
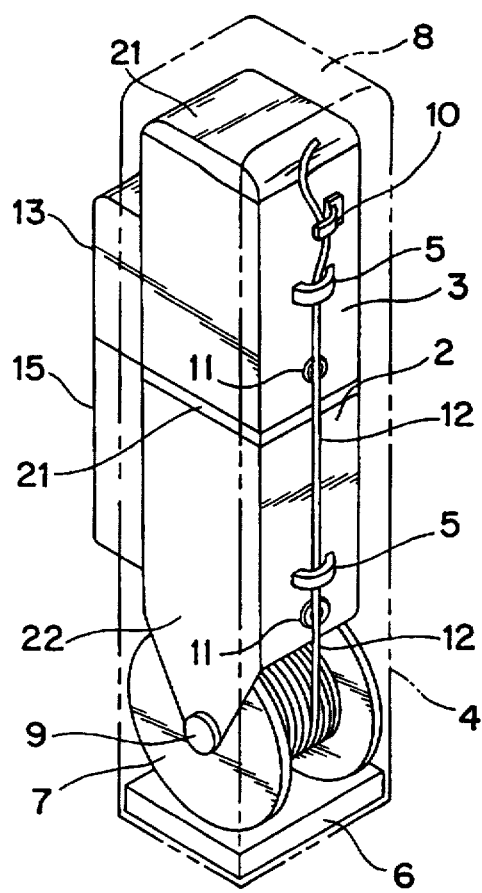
FIG. 1 is a perspective view of the present invention showing the outer casing in phantom lines.

Referring now to the drawings in greater detail, FIG. 1 shows a perspective view of the present invention. Dual hollow containers 2,3 are mounted one above the other. One of the container will be filled with a first solution such as peroxide, and the second chamber will be filled with a different solution such as fluoride. The chambers should be individual chambers so the solution in each chamber will not mix with the solution in the other chamber. A lid 21 can be provided for each chamber to allow filling them with the individual solutions. The chambers 2,3 can be stacked together by any conventional method.

Each chamber will have an orifice 11 which will allow the solution in each chamber to be forced out of the chamber onto the dental floss 12, as will be explained in more detail below. The orifices 11 are preferably provided on the side of the respective chambers, however, the location is not critical as long as the respective solutions can be applied to the dental floss.

Each chamber is also provided with a guide 5 for the floss so the floss will be directed pass the orifices 11. The guides could be a strap portion which is connected at both ends to the walls of the containers 2,3 or the straps could have only one end attached to the walls so the floss could be passes under the free end of the straps. If the straps are connected at both ends to the walls, the floss will be threaded through the opening between the straps and the walls in order to pass by the orifices 11.

In addition, a dental floss cutter 10 could be provided at the upper portion of the chamber 3 to cut off a supply of floss. The cutter 10 is a conventional cutter used with most dental floss containers and, therefore, will not be described further.

At the bottom of the container 2 is a flange portion 22, to which is mounted an axle 9 which will hold a spool of dental floss 12. In addition, an outer casing 4 may be provided to house the containers 2,3. The outer casing may have a lid 8 which can be pivotally attached to the casing by any conventional means such as, but not limited to, a living hinge. Secured to the bottom of the outer casing 4 is an absorbent pad such as, but not limited to a sponge, which will soak up any excess solution.

Figure 2:
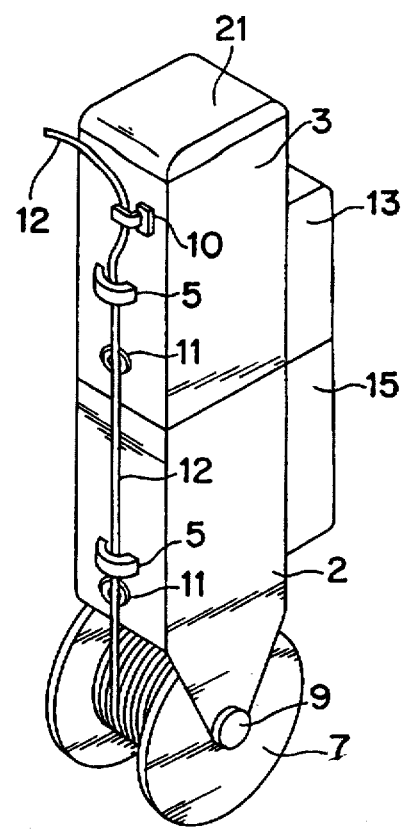
FIG. 2 is a perspective view of the present invention.
Figure 3:
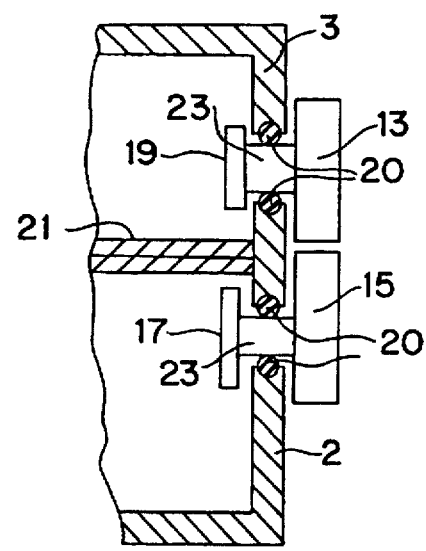
FIG. 3 is a partial cross-sectional view of the plungers of the present invention.

As shown more clearly in FIGS. 2 and 3, secured to the opposite side from the orifices 11, is a plunger apparatus 17, 19, 23 which will be used to force the solutions from their respective chambers. Each plunger will have a handle portion 13, 15 (see FIG. 3) which the user can push with one or more fingers, a stem portion 23 and a plunger head 17, 19. The stems 23 will extend through apertures in the sides of the respective chambers 2,3 and will engage O-rings 20 in order to seal the apertures from leaking. Also, it should be noted that the O-rings could be mounted on the stems 23 and engage the walls of the apertures in order to seal the apertures from leaking.

In order to use the dental floss dispenser, a user would press one or both of the handle portion 13, 15 to dispense a small amount of solution through the apertures 11 and unto the dental floss 12 which has been threaded through the guide straps 5. The user would then select a desired amount of dental floss and cut it off using the cutter 10. Any excess solution would be absorbed by the pad 6 in the bottom of the container 4.

The containers 2, 3, the thread guides 5, and the lids 21 would be preferably made by blow molding from polyethylene plastic. This type of plastic is flexible enough to dispense both liquids, while being rigid enough to hold the spool of dental floss.

Blow molding is an inexpensive process which uses a parison (hollow tube) of plastic, and at minimum a two part mold. The hollow plastic tube (parison) is heat softened and a cavity (within the two part mold) is placed around the tube. The mold pinches off one end of the tube while hot air is blown into the other end of the plastic tube. The tube "blows up" like a balloon against the mold. This means that the blown plastic takes on the shape of the mold it was formed against.

The two part mold is then opened up and the article ejected and allowed to cool and harden. Second stage cutting and trimming follows to give the part a finished look. Some of the second stage work is performed by hand while other portions may be done by machine depending on the exact nature of the part being worked on.

Most blow molders like to use polyethylene plastic because it has a waxy feel to it and slides well within the mold, although other materials may be used.

The outside case 4, and the plungers 13, 15 would be made from ABS plastic using an injection molding process. Injection molding is a plastic molding procedure whereby heat softened plastic material is forced under very high pressure into a metal cavity mold which is relatively cool. Acceptable metals for the mold are aluminum and steel. The inside cavity of the mold is comprised of two or more halves, and is the same desired shape as the product to be formed. High pressure hydraulics are used to keep the mold components together during the actual injection phase of the molding process. The injected plastic is allowed to cool and harden. The hydraulics holding the multiple component cavity together are released, the halves of the mold are separated and the solid formed plastic item is removed. Injection molding can be a highly automated process and is capable of producing extremely detailed parts at a very cost effective price.

Although preferred methods of making the invention have been disclosed, it should be understood that other methods could be used without departing from the scope of the invention.

Although the Fluoride/Peroxide Dental floss Container and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A container for dispensing dental floss comprising:
   at least two chambers,
   each of said chambers containing an antiseptic solution,
   means on at least one of said chambers for holding a spool of dental floss,
   each of said chambers containing an orifice means for permitting said solutions to be dispensed to the outside of said chambers,
   means for guiding said dental floss passed said orifice means,
   each of said chambers having plunger means for extracting solutions within said chambers through said orifice means,
   whereby a user may use said plunger means to coat said dental floss with said antiseptic solutions prior to using said dental floss.

2. The container for dispensing dental floss as claimed in claim 1, wherein means for guiding said dental floss passed said orifice means is at least one strap attached to an outside surface of at least one of said chambers.

3. The container for dispensing dental floss as claimed in claim 1, wherein each of said plunger means comprises a handle portion, a stem portion and a head portion,
   said handle portion being disposed on an outside of the respective chambers,
   said stem portion passing through an aperture in the respective chambers, and
   said head portion being disposed within the respective chambers.

4. The container for dispensing dental floss as claimed in claim 3, wherein each said aperture has a seal means for preventing leakage of solution through said apertures.

5. The container for dispensing dental floss as claimed in claim 4 wherein said seal means is at least one O-ring which engages said stem portion.

6. The container for dispensing dental floss as claimed in claim 1, wherein said container has a cutting means for cutting off a selected amount of said dental floss.

7. The container for dispensing dental floss as claimed in claim 1, wherein said at least two chambers are disposed within an outer container.

8. The container for dispensing dental floss as claimed in claim 7, wherein said outer container has a lid hingedly connected to a top of said outer container.

9. A container for dispensing dental floss comprising:
   at least two chambers,
   each of said chambers containing an antiseptic solution,
   means on at least one of said chambers for holding a spool of dental floss,
   each of said chambers containing an orifice means for permitting said solutions to be dispensed to the outside of said chambers,
   means for guiding said dental floss passed said orifice means,
   each of said chambers having plunger means for extracting solutions within said chambers through said orifice means, and
   wherein said at least two chambers are disposed within an outer container, and
   wherein said outer container has an absorption means disposed in a bottom of said outer container for absorbing any excess solution,
   whereby a user may use said plunger means to coat said dental floss with said antiseptic solutions prior to using said dental floss.

10. The container for dispensing dental floss as claimed in claim 9, wherein means for guiding said dental floss passed said orifice means is at least one strap attached to an outside surface of at least one of said chambers.

11. The container for dispensing dental floss as claimed in claim 9, wherein each of said plunger means comprises a handle portion, a stem portion and a head portion,
    said handle portion being disposed on an outside of the respective chambers,
    said stem portion passing through an aperture in the respective chambers, and said head portion being disposed within the respective chambers.

12. The container for dispensing dental floss as claimed in claim 11, wherein each said aperture has a seal means for preventing leakage of solution through said apertures.

13. The container for dispensing dental floss as claimed in claim 12 wherein said seal means is at least one O-ring which engages said stem portion.

14. The container for dispensing dental floss as claimed in claim 9, wherein said container has a cutting means for cutting off a selected amount of said dental floss.

15. The container for dispensing dental floss as claimed in claim 9, wherein said outer container has a lid hingedly connected to a top of said outer container.

* * * * *